(12) United States Patent
Chuang

(10) Patent No.: US 7,381,849 B1
(45) Date of Patent: Jun. 3, 2008

(54) SYNTHESIS OF ASYMMETRIC TETRACARBOXYLIC ACIDS AND DIANHYDRIDES

(75) Inventor: Chun-Hua Chuang, Brecksville, OH (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/890,104

(22) Filed: Jul. 19, 2007

Related U.S. Application Data

(63) Continuation-in-part of application No. 11/378,553, filed on Mar. 8, 2006, which is a continuation-in-part of application No. 10/897,279, filed on Jul. 23, 2004, now Pat. No. 7,015,304.

(51) Int. Cl.
| | |
|---|---|
| *C07C 45/00* | (2006.01) |
| *C07C 49/00* | (2006.01) |
| *C07C 51/16* | (2006.01) |
| *C07C 59/76* | (2006.01) |

(52) U.S. Cl. ............... 568/319; 568/325; 568/335; 562/407; 562/460

(58) Field of Classification Search .............. None
See application file for complete search history.

(56) References Cited

U.S. PATENT DOCUMENTS 3,940,426 A * 2/1976 Itatani et al. .......... 549/241
4,294,976 A * 10/1981 Itatani et al. .......... 560/76
4,958,002 A 9/1990 Imatani .............. 528/353
5,258,530 A 11/1993 Katsura .............. 549/241

OTHER PUBLICATIONS

Zhurnal Prikladnoi Khimii (Sankt-Peterburg, Russian Federation) (1970), 43(3), 620-7; CAS online citation 73:45059 [retrieved Jan. 17, 2008] from STN; Columbus, OH, USA.*
Compt. Rend. (1965), 260(3), 923-5 both teach 2,3,3',4'-tetramethylbenzophenone, CAS online citation 63:38832 [retrieved Jan. 17, 2008] from STN; Columbus, OH, USA.*

* cited by examiner

*Primary Examiner*—Karl Puttlitz
(74) *Attorney, Agent, or Firm*—Kent N. Stone; James V. Tura

(57) ABSTRACT

This invention relates to the compositions and processes for preparing 2,3,3',4'-tetramethylbenzophenone and asymmetrical dianhydrides such as 2,3,3',4' benzophenone dianhydride (a-BTDA), and 3,4'-(hexafluoroisopropylidene) diphthalic anhydride (a-6FDA). a-BTDA is prepared by Suzuki coupling with catalysts from a mixed anhydride of 3,4-dimethylbenzoic acid and 2,3-dimethylbenzoic acid with a respective 2,3-dimethylphenylboronic acid and 3,4-dimethyl phenylboronic acid to form 2,3,3',4'-tetramethylbenzophenone which is oxidized to 2,3,3',4'-benzophenonetetracarboxylic acid followed by cyclodehydration to obtain a-BTDA. The a-6FDA was prepared by nucleophilic trifluoromethylation of 2,3,3',4'-tetramethylbenzophenone with trifluoromethyltrimethylsilane to form 3,4'-(trifluoromethylmethanol) bis(o-xylene) which is converted to 3,4'-(hexafluoroisopropylidene-bis(o-xylene). The 3,4'-(hexafluoroisopropylidene)-bis(o-xylene) is oxidized to the corresponding tetraacid followed by cyclodehydration to yield a-6FDA.

9 Claims, No Drawings

SYNTHESIS OF ASYMMETRIC TETRACARBOXYLIC ACIDS AND DIANHYDRIDES

RELATED U.S. APPLICATION

This application is a continuation-in-part of co-pending application, Ser. No. 11/378,553 filed Mar. 8, 2006, which is a continuation-in-part of application Ser. No. 10/897,279 filed Jul. 23, 2004 and issued as U.S. Pat. No. 7,015,304 on Mar. 21, 2006.

ORIGIN OF INVENTION

The invention described herein was made by an employee of the United States Government and may be manufactured and used by or for the Government for governmental purposes without the payment of any royalties thereon or therefor.

FIELD OF THE INVENTION

This invention relates to the composition and the process for preparing asymmetric tetracarboxylic acids, the corresponding dianhydrides, and the intermediates of said dianhydrides namely, 2,3,3',4'-biphenyldianhydride (a-BPDA), 2,3,3',4'-benzophenone dianhydride (a-BTDA), 3,4'-methylenediphthalic anhydride (a-MDPA) and 3,4'-(hexafluoroisopropylidene)diphthalic anhydride (a-6FDA). These tetracarboxylic acids and dianhydrides were prepared by cross-coupling isomers of dimethylphenylboronic acid and o-xylene derivatives via Suzuki coupling with various catalysts to form 2,3,3',4'-tetramethylbiphenyl and 2,3,3',4'-tetramethylbenzophenone. The asymmetrical tetramethylbiphenyl and the tetramethylbenzophenone were oxidized to the corresponding tetracarboxylic acids which were then converted to asymmetrical 2,3,3',4'-biphenyl dianhydride and 2,3,3',4'-benzophenone dianhydride. In addition, the benzophenone tetracarboxylic acid can be reduced by hydrazine hydrate to 3,4'-methylene diphthalic tetracarboxylic acid which is converted to the corresponding 3,4'-methylenediphthalic anhydride. The unique feature of this invention is that it allows for the production of a series of asymmetric dianhydrides, not only a-BPDA, but also a-BTDA, a-MDPA and a-6FDA. This capability of producing a-BPDA, a-BTDA, a-MDPA and a-6-FDA, will usher in innovation for the preparation of high $T_g$, low-melt viscosities and colorless polyimides with interesting and novel properties for aerospace and electronic applications.

More specifically, this invention relates to the process for preparing the intermediate 2,3,3',4'-tetramethylbenzophenone and the compositions derived from said 2,3,3',4'-tetramethyl benzophenone, namely: 2,3,3',4' benzophenonetetracarboxylic acid and 3,4'-(hexafluoroisopropylidene) diphthalic acid and the corresponding asymmetric anhydrides. For example, thermosetting polyimides derived from asymmetrical 2,3,3',4'-biphenyl dianhydride (a-BPDA) have been shown to produce low melt viscosity and high $T_g$ polyimides for resin transfer molding; see the Proceedings of the SAMPE Symposium, Long Beach, Calif., May 1-5, 2005. Recently, it was discovered that asymmetric 2,3,3',4'-biphenyl dianhydride (a-BPDA) reacted with diamines and an endcap to produce polyimides with lower-melt viscosities and higher glass transition temperatures ($T_g$) than the symmetrical 3,3',4,4'-biphenyl dianhydride (s-BPDA); see High Performance Polymers, Vol. 13, 355 (2001), and Vol 15, 375 (2003).

Specifically, this invention particularly relates to novel processes for the preparation of two asymmetric dianhydrides, namely, 2,3,3',4'-benzophenone dianhydride (a-BTDA) and 3,4'-(hexafluoroisopropylidene)diphthalic anhydride (a-6FDA). The a-BTDA was prepared by Suzuki coupling with palladium catalysts from 3,4-dimethylphenylboronic acid or 2,3-dimethylphenylboronic acid and a mixed anhydride of 2,3-dimethylbenzoic acid and 3,4-dimethylbenzoic acid to form 2,3,3',4'-tetramethylbenzophenone which was then oxidized to 2,3,3',4'-benzophenonetetracarboxylic acid followed by cyclodehydration to obtain a-BTDA. The a-6FDA tetracid was prepared by nucleophilic trifluoromethylation of 2,3,3',4'-tetramethylbenzophenone with trifluoromethyltrimethylsilane to form 3,4'-(trifluoromethylmethanol)-bis(o-xylene), which is converted to 3,4'-(hexafluoroisopropylidene)-bis(o-xylene). The 3,4'-(hexafluoroisopropylidene)-bis(o-xylene) is oxidized to the corresponding tetraacid followed by cyclodehydration to yield a-6FDA. Thermoplastic and thermoset polyimides and co-polyimides derived from a-BTDA and a-6FDA can be made from a mixture of one or more of these dianhydrides (or the corresponding acid esters or isoimide derivatives) and one or more diamine with or without a monofunctional reactive endcap (such as nadic or phenylethynyl groups) or non-reactive terminating endcap (e.g. phthalic anhydride or aniline) in stoichiometric or non-stoichiometric amounts in a solvent or neat without solvent.

BACKGROUND OF THE INVENTION

Currently, for example, asymmetrical a-BPDA is being prepared from o-xylene via an oxidative coupling reaction which essentially yields a mixture of 3,3',4,4'-biphenyl dianhydride (s-BPDA) and a minor product (2-6%) of a-BPDA. Consequently, a-BPDA is being produced in limited quantity and therefore is not commercially available in sufficient amounts, despite an enormous interest is preparing polyimides using a-BPDA. This invention discloses alternative and more efficient processes for producing asymmetric 2,3,3',4'-biphenyl dianhydride (a-BPDA), 2,3,3',4'-benzophenone dianhydride (a-BTDA), 3,4'-methylenediphthalic anhydride (a-MDPA) and 6FDA.

The prior art (U.S. Pat. No. 3,940,426, UBE Industries) process for making a-BPDA relies on oxidative coupling of o-xylene or o-phthalate with an organic acid salt of palladium under oxygen pressure to produce a mixture of symmetrical and unsymmetrical intermediates which are oxidized and cyclodehydrated to form a mixture of a-BPDA and s-BPDA. This mixture requires the additional process of separating the two isomers.

U.S. Pat. No. 4,294,976 discloses a process for preparing a mixture of biphenyltetracarboxylic acids (3,3',4,4'-isomer, 2,3,3',4'-isomer and 2,2',3,3' isomer) via an oxidative coupling of either o-xylene or o-phthalate in the presence palladium catalyst followed by hydrolysis. The mixture of isomeric biphenyltetracarboxylic acids were then subjected to fractionally recrystallization to obtain the corresponding 2,3,3',4'- (minor amount) and 3,3',4,4'- (major amount) and minute amounts of 2,2',3,3'-biphenyldianhydrides.

U.S. Pat. No. 4,958,002 discloses a dehydration process to obtain 3,3',4,4'-biphenyl dianhydride after the corresponding 3,3',4,4'-biphenyltetracarboxylic acid was isolated from 2,3, 3',4'-biphenyltetracarboxylic acid. U.S. Pat. No. 5,258,530 (Mitsibishi) describes a coupling reaction of phthalic anhydride to form a mixture of 2,3,3',4'- (major) and 2,3,3',4'- (minor) biphenyl dianhydrides. U.S. Patent Publication No. 0088120 A1 (2003) discloses a process for producing predominately 2,3,3',4'-biphenyl dianhydride (a-BPDA) with a minor amount of 3,3',4,4'-biphenyldianhydride (s-BPDA) using palladium and copper catalyst with bidentate ligand. These prior art processes all yield mixtures of asymmetrical dianhydrides together with symmetrical dianhydrides, which then requires the separation of these isomers. In comparison, this invention discloses asymmetrical coupling of dimethylphenylboronic acid with o-xylene derivatives to provide asymmetrical dianhydrides without contamination by the symmetrical dianhydrides.

SUMMARY OF THE INVENTION

By employing a cross-coupling reaction (Suzuki coupling) with 3,4-dimethyl or 2,3-dimethylphenylboronic acid and 3- or 4-substituted o-xylenes in the presence of catalysts, this invention exclusively produces asymmetric precursors; namely, 2,3,3',4'-tetramethylbiphenyl and 2,3,3',4'-tetramethylbenzophenone. These precursors are subsequently oxidized to produce asymmetric tetracarboxylic acids which are converted to the corresponding dianhydrides.

The dianhydrides of this invention are useful in preparing polyimides which comprise an important class of polymers because of their desirable characteristics i.e. low dielectric constant, high breakdown voltage, good wear resistance, radiation resistance, inertness to solvents, good adhesion properties, hydrolytic stability, low thermal expansion, long-term stability, and excellent mechanical properties. Specifically, high temperature polyimides, such as PMR-15, are extremely valuable particularly for aerospace applications. However, making components from these polymers via prepreg process is labor intensive and expensive. Resin Transfer Molding (RTM) is a more cost-effective alternative to making aerospace components and has been successfully deployed with lower temperature polymers such as the epoxies and bismaleimides (BMI).

A unique feature of this invention is the processes for preparing novel asymmetrical dianhydrides, namely, a-BTDA and a-6FDA, without the contamination of their symmetrical isomers (s-BTDA and s-6FDA). The a-BTDA and a-6FDA can be used to formulate or prepare polyimides with low-melt viscosities without the use of high boiling point organic solvents such as N-methyl-pyrrolidinine (NMP) whereas the conventional polyimides derived from s-BTDA and s-6FDA usually afford high viscosity.

Accordingly, it is a primary object of this invention to provide a process for preparing asymmetric dianhydrides, namely: 2,3,3',4'-benzophenone dianhydride (a-BTDA) and 3,4'-(hexafluoroisopropylidene)diphthalic anhydride (a-6FDA).

It is another object of this invention to provide a process for preparing the intermediate 2,3,3',4'-tetramethylbenzophenone from which is derived 2,3,3',4'-benzophenonetetracarboxylic acid and 3,4'-(hexafluoroisopropylidene)diphthalic acid and the corresponding asymmetric anhydrides (a-BTDA and a-6FDA).

It is another object of this invention to provide processes for the preparation of a-BTDA and a-6FDA, and the compositions derived from said processes.

It is another object of this invention to provide processes for preparing asymmetrical tetracarboxylic acids and the corresponding dianhydrides (a-BTDA and a-6FDA) useful in producing polyimides having lower-melt viscosities and high glass transition temperatures ($T_g$).

It is a further object of this invention to provide processes for the synthesis of a-BTDA and a-6FDA by cross-coupling dimethylphenylboronic acid with substituted o-xylenes to produce asymmetric precursors which are further reacted to form the corresponding tetracarboxylic acids and subsequently converted to the corresponding asymmetric dianhydrides.

These and other objects will become more apparent from a further and more detailed description of the invention.

DETAILED DESCRIPTION OF THE PREFERRED EMBODIMENTS

As shown in the reactions of Scheme I, the asymmetric dianhydrides are obtained by cross-coupling o-xylene derivatives (I) and (II), if (I) is a 3-boron substituted o-xylene, then (II) is a 4-substituted o-xylene, or if (I) is a 4-boron substituted o-xylene, then (II) is a 3-substituted o-xylene derivative. 2,3,3',4'-biphenyl dianhydride (a-BPDA) is prepared by cross-coupling (I) and (II), where X is selected from the group consisting of F, Cl, Br, I, $OSO_2CF_3$, $OSO_2CH_3$ and Y is $(OH)_2$, or $(OR)_2$, where R is a lower alkyl group such as $CH_3$, $C_2H_5$, i-Pr, in order to form the asymmetrical 2,3,3',4'-tetramethylbiphenyl (III) in a common organic solvent, e.g. toluene, N,N-dimethyformamide (DMF), dimethoxyethane (DME), 1,4-dioxane, tetrahydrofuran (THF), anisole, or aqueous solution with or without phase transfer catalysts in the presence of palladium or nickel catalysts, either with or without a co-catalysts or co-ligands, such as $Pd(PPh_3)_4$, $Pd(OAc)_2$, $Pd(PPh_3)_2 Cl_2$, $PdCl_2(CH_3CN)_2$, $Pd(dba)_2/P(t-Bu)_2$, $Pd_2(dba)_2/[t-Bu)_2PH]$ $BF_4$, $NiCl_2(PPh_3)_2$, $NiCl_2(PCy_3)_2$, $NiCl_2(dppf)$, $NiCl_2$ (dppe), $NiCl_2(dppb)$, and their corresponding polymer bound palladium or nickel catalysts.

Compound (III) is oxidized by potassium permanganate ($KMnO_4$), chromium trioxide ($CrO_3$), or by other oxidation methods such as low or high pressure nitric acid oxidation, catalytic oxidation, in air or in oxygen to form the 2,3,3', 4'-biphenyltetracarboxylic acid (IV), which upon dehydration e.g. by acetic anhydride or thermal dehydration, yields 2,3,3',4'-biphenyl dianhydride (V). Alternatively, compounds (I) and (II) are cross-coupled with carbon monoxide gas in the presence of the Pd or nickel catalysts to form the asymmetrical 2,3,3',4'-tetramethylbenzophenone (VI), which is further oxidized e.g. by $KMnO_4$, $CrO_3$, nitric acid oxidation, or with other known catalytic oxidation methods in air or oxygen to form 2,3,3',4'-benzophenonetetracarboxylic acid (VII) which is then dehydrated by acetic anhydride or thermally cyclodehydrated to yield 2,3,3',4'-benzophenone dianhydride (VIII). Alternatively, 2,3,3',4'-benzophenonetetracarboxylic acid (VII) is reduced by hydrazine to form 3,4'-methylenediphthalic acid (IX), which upon dehydration e.g. by acetic anhydride yields 3,4'-methylenediphthalic anhydride (X).

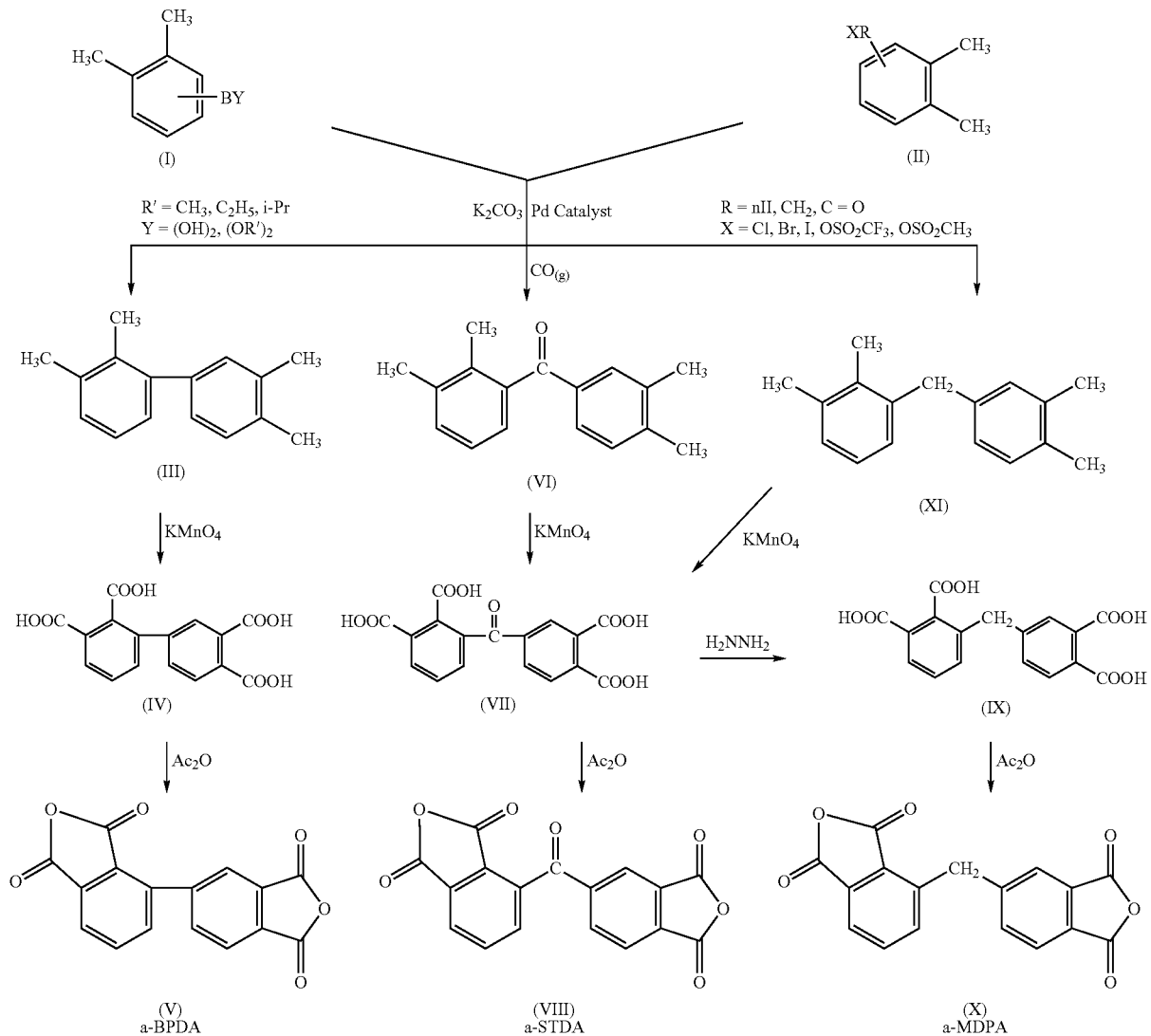

Scheme I Synthesis of Asymmetrical Dianhydrides from o-xylene Derivatives

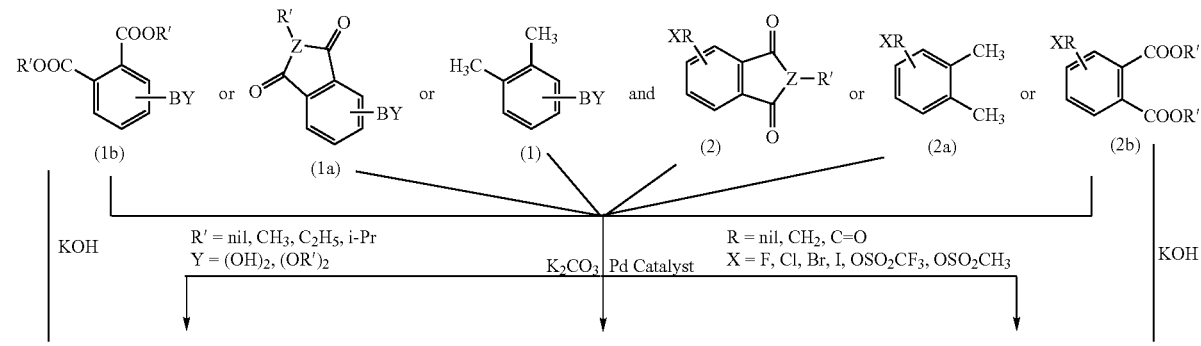

Scheme II Synethesis of Asymmetrical Dianhydride between o-Xylene Derivatives and Phthalic Anhydride or Phthalimide Derivatives

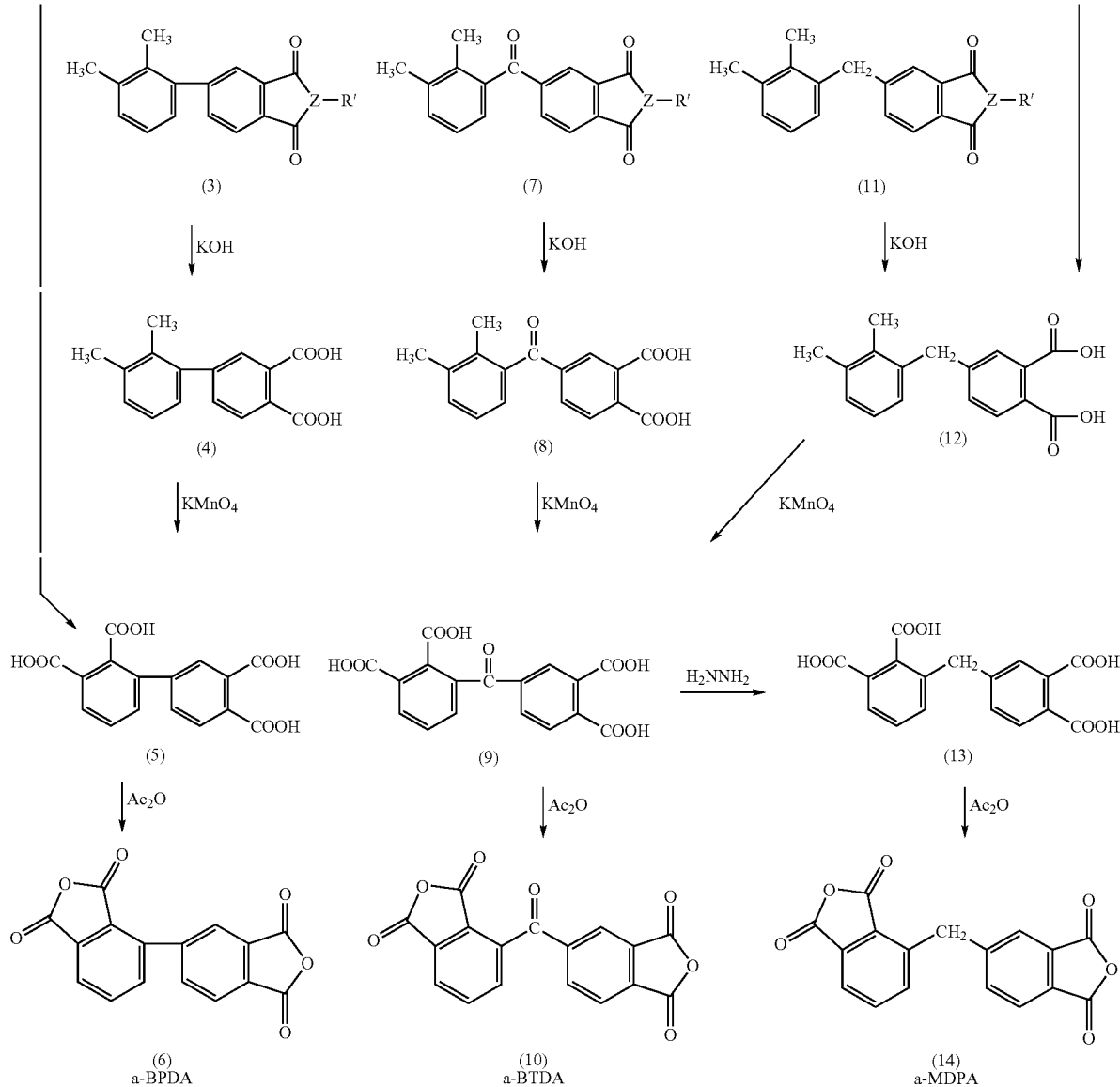

(6) a-BPDA
(10) a-BTDA
(14) a-MDPA

In Scheme II, a similar Suzuki cross-coupling reaction is carried out between 3- or 4-boron-substituted o-xylene (1), boron-substituted phthalic derivative (1a) or boron-substituted phthalic diester (1b), and 4- or 3-halo-substituted phthalic anhydrides, phthalic ester or phthalimides (2), or diesters of phthalic acid respectively, to produce the coupled asymmetrical 4-(2,3-dimethylphenyl)phthalic anhydride, phthalic ester or phthalimide (3). Compound (3) can be hydrolyzed e.g. by potassium hydroxide, followed by oxidation e.g. by $KMnO_4$, $CrO_3$ and other oxidizing methods such as low or high pressure nitric acid or with catalytic oxidation in air or oxygen to afford 2,3,3',4'-biphenyl tetracarboxylic acid (5), which upon dehydration e.g. with acetic anhydride or thermal cyclodehydration to yield 2,3,3',4'-biphenyl dianhydride (a-BPDA). In the presence of carbon monoxide gas, 2,3,3',4'-benzophenone dianhydride (10), (a-BTDA) is produced by similar routes from compounds (1) and (2) via compounds (7), (8) and (9) as shown in this reaction.

Alternatively, 2,3,3',4'-benzophenonetetracarboxylic acid (9) is obtained through $KMnO_4$ oxidation of (2,3-dimethylphenyl)-α-methylphthalic acid (12) after hydrolysis or from the corresponding phthalimide (11) via the Suzuki coupling of an o-xylene derivative (1) with α-halomethylphthalic anhydride or α-halomethylphthalimide (2) with palladium or nickel catalysts. 2,3,3',4'-benzophenone tetracarboxylic acid (9) can be reduced by hydrazine to 3,4'-methylene diphthalic acid (13), which upon dehydration yields 3,4'-methylene diphthalic anhydride (14) (a-MDPA). In the cross-coupling reactions, X is selected from the group consisting of a halogen e.g. Cl, F, Br, I, or $OSO_2CF_3$ and $OSO_2CH_3$ Y is either $(OH)_2$, or $(OR)_2$. Z is either oxygen or nitrogen. R is —$CH_2$, —C=O, or nil. R' is a lower alkyl such as $CH_3$, or $C_2H_5$, and B is boron.

The dianhydrides prepared by these processes are particularly useful in preparing polyimides from one or more of a combination of reactants comprising dianhydrides selected from the group consisting of 2,3,3',4'-biphenyldianhydride (a-BPDA), 2,3,3',4'-benzophenone dianhydride (a-BTDA), and 3,4'-methylenediphthalic anhydride (a-MDPA), with at least one multifunctional amine such as diamines and an endcap that can be melt-processed at temperatures between 232-270° C. (450-520° F.), without any solvent. The imide oligomers of this reaction have low-melt viscosities of 1-60 poise at 260-280° C. These imide oligomers are amenable to TRM, VARTM or resin infusion processes at 260-280° C. to product high quality polymer composites comprising carbon, glass, quartz or synthetic fibers for use at temperatures ranging up to about 550° to 650° F.

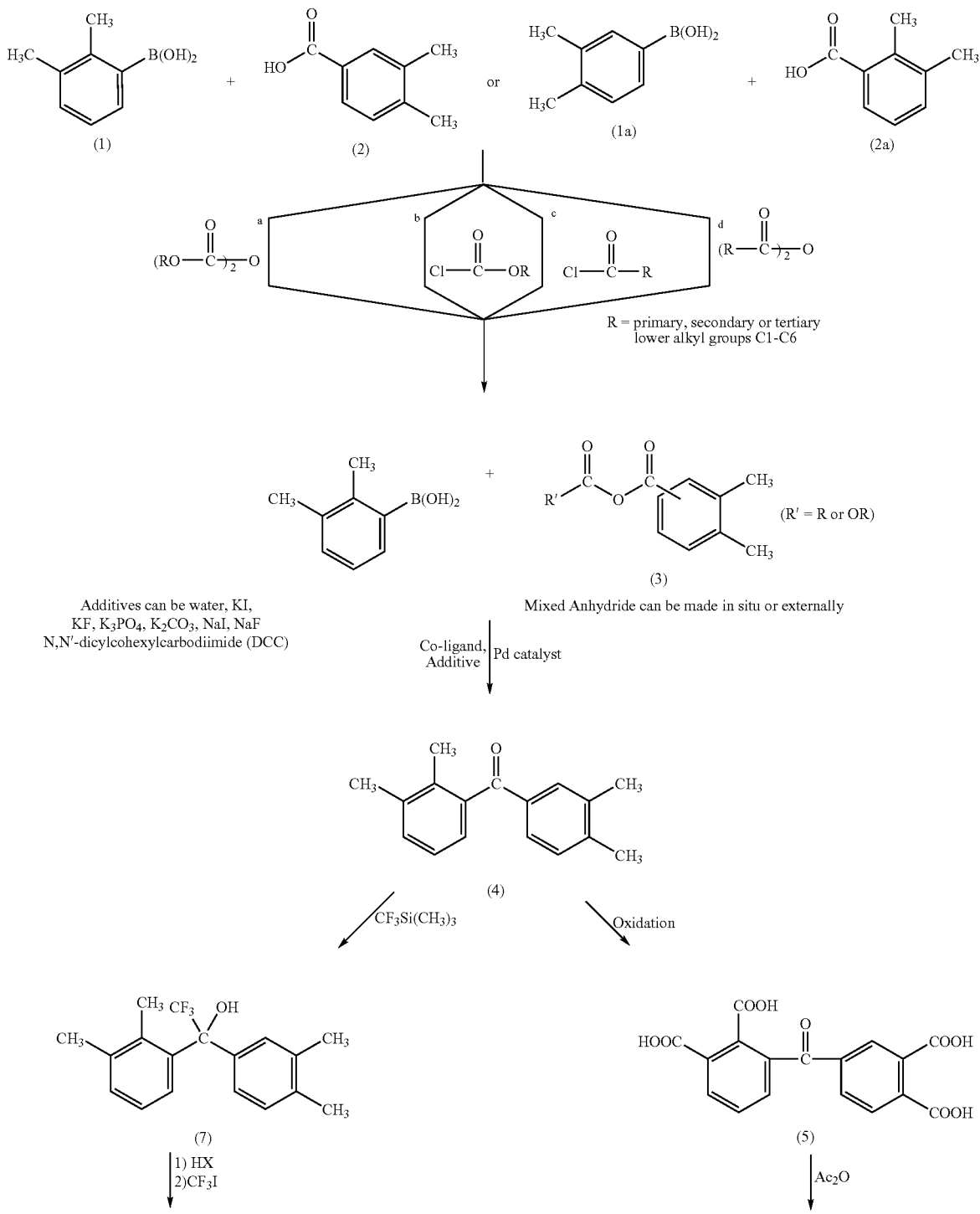

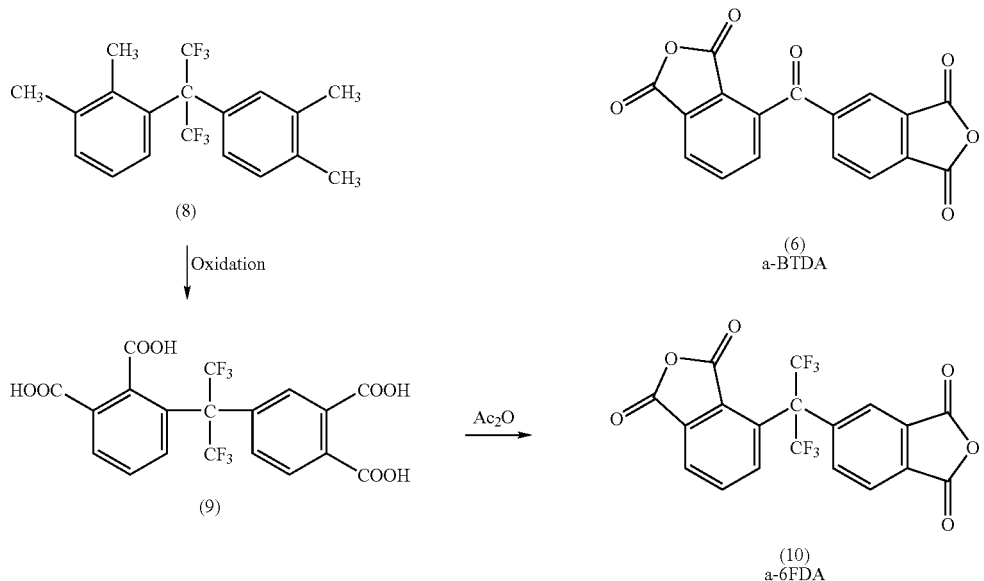
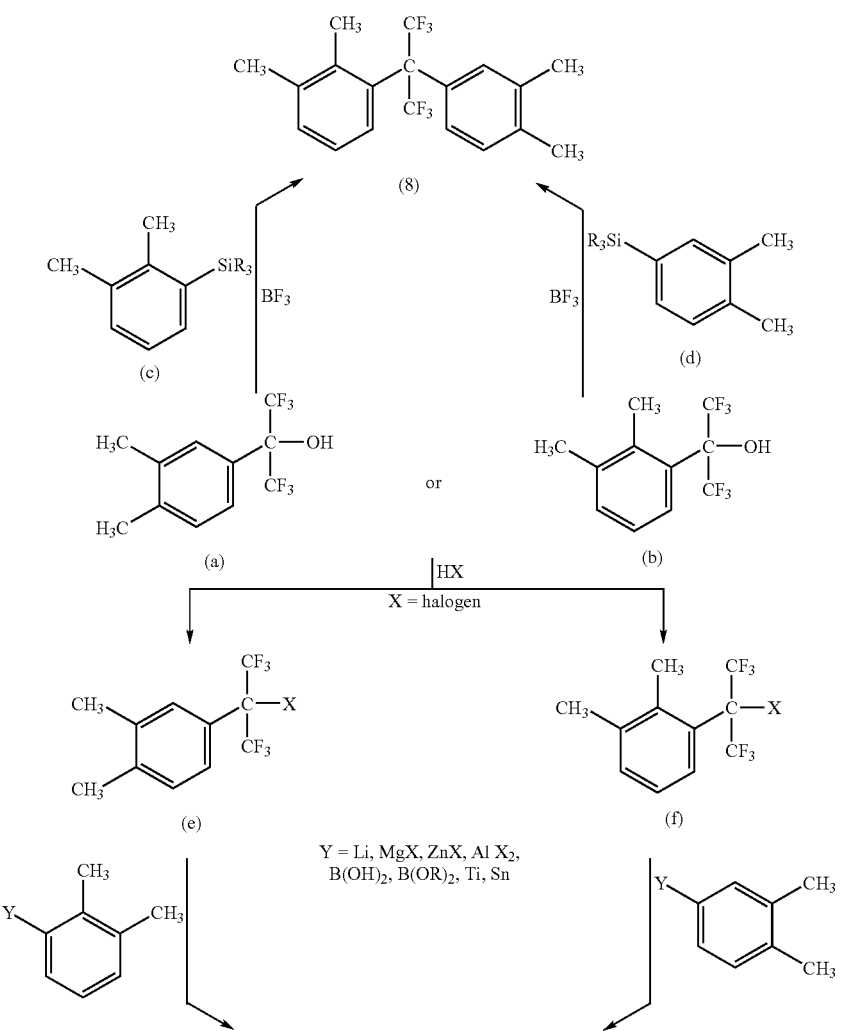
Scheme IV Alternative Synthesis of a-6FDA
Y = Li, MgX, ZnX, Al X$_2$, B(OH)$_2$, B(OR)$_2$, Ti, Sn

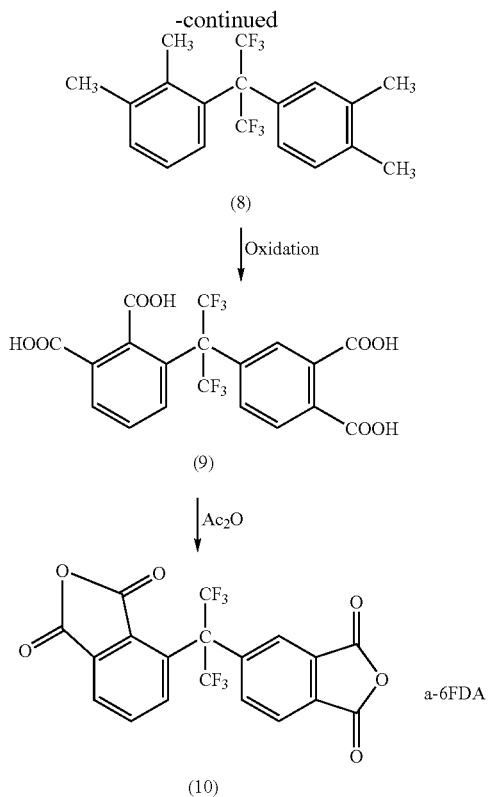

As specifically illustrated in Schemes III and IV, the invention exclusively provides processes for preparing asymmetrical 2,3,3',4'-benzophenone dianhydride (a-BTDA) and asymmetrical 3,4'-(hexafluoroisopropylidene)diphthalic anhydride (a-6FDA) without the complicated process of separating isomers. 2,3,3',4'-benzophenone dianhydride (a-BTDA) is prepared by employing the cross-coupling of specific pair of dimethylphenylboronic acid with a mixed anhydride of dimethylbenzoic acid, generated in situ or prepared externally, to obtain the intermediate 2,3,3',4'-tetramethylbenzophenone (4). The mixed dianhydride can be prepared by reacting 3,4-dimethylbenzoic acid or 2,3-dimethylbenzoic acid with either a dialkyl dicarbonate, alkyl chloroformate, alkyl acid halides (acid chloride preferred) or alkyl dianhydrides where the alkyl groups includes primary, secondary and tertiary alkyl groups of $C_1$-$C_6$. The catalysts for the cross-coupling reaction includes, but is not limited to Pd(PPh$_3$)$_4$, Pd(PPh$_3$)$_2$ Cl$_2$, Pd(PCy$_3$)$_2$, Pd(OAc)$_2$, PdCl$_2$(CH$_3$CN), and Pd(dba)$_2$/p(t-Bu)$_2$. The co-catalysts or co-ligands include but not limited to PPh$_3$, PCy$_3$, P(p-MeOC$_6$H$_5$)$_3$, P(o-Tol)$_3$, and 1,1'-bis(diphenylphosphino)ferrocene (DPPF). Other additives for the cross-coupling reaction can include water, NaI, NaF, Na$_2$CO$_3$, KI, KF, K$_2$CO$_3$, K$_3$PO$_4$ and dicyclohexylcarbodiimide (DCC). 2,3,3',4'-tetramethylbenzophenone is reacted with trifluoromethyltetramethylsilane CF$_3$Si(CH$_3$)$_3$ and further converted to 3,4'-(hexafluoroisopropylidene)bis-o-xylene (8).

Alternatively, 3,4'-(hexafluoroisopropylidene)bis-o-xylene (8) is also prepared from two different routes as shown in Scheme IV. A) Via the coupling of either 2-(3,4-dimethylphenyl)-hexafluoro-2-propanol (a) or 2-(2,3-dimethylphenyl)-hexafluoro-2-propanol (b) with respective trialkylsilane derivatives of o-xylene (c) and (d). B) By converting (a) and (b) to their corresponding halides (e) and (f) and then coupled with 3- or 4-substituted o-xylene.

2,3,3',4'-tetramethylbenzophenone (4) and 3,4'-(hexafluoroisopropylidene)bis-o-xylene (8) are oxidized by potassium permanganate (KMn O)$_4$, chromium trioxide (CrO$_3$), or by other oxidation methods, such as nitric acid oxidation, or catalytic oxidation in air or oxygen in the presence of catalysts to obtain the corresponding 2,3,3',4'-benzophenone tetracarboxylic acid (5) and 3,4'-(hexafluoroisopropylidene) diphthalic acid (9), respectively. The tetracarboxylic acids (5) and (9) are subsequently reacted with either acetic anhydride or propionic dianhydride, or thermally cyclodehydated to obtain the corresponding 2,3,3',4'-benzophenone dianhydride (a-BTDA) or 3,4'-(hexafluoroisopropylidene) diphthalic anhydride (a-6FDA).

EXAMPLE I

Synthesis of 2,3,3',4'-tetramethylbenzophenone (4)

To a 250 ml 3-necked round-bottom flask, 2,3-dimethylphenylboronic acid (3.6 g. 24 mmol). 3,4-dimethylbenzoic acid (3.0 g. 20 mmol), a selected palladium catalyst (0.6 mmol), dimethyl dicarbonate (2.7 g. 30 mmol) and potassium carbonate (6.22 g. 45 mmol) were mixed with 150 ml of dry dioxane. The reaction mixture was heated at 80° C. overnight to become a viscous reaction mixture. 20 ml of water was added to dissolve the heterogeneous reaction mixture, and dioxane was evaporated to dryness. The aqueous solution was extracted with 20 ml of ethyl acetate, dried over anhydrous magnesium sulfate and then evaporated to dryness. The crude product was purified by silica gel column chromatography eluted by hexane/ethyl acetate=20/80 to afford 2.0 g (33%) of the product.

Synthesis of 2,3,3',4'-benzophenonetetracarboxylic acid (5)

2,3,3',4'-tetramethylbenzophenone (2.0 g. 8.4 mmol) and potassium permanganate (5.3 g. 33.6 mmol) were mixed in 25 ml of water in a 100 ml round-bottom flask and the reaction mixture turned purple. The reaction mixture was heated at 90° C. overnight. The reaction mixture turned brown, and the brown MnO$_2$ precipitate was filtered and removed. The aqueous solution was evaporated to dryness to afford 2.5 g (80%) of the desired tetraacid.

Synthesis of 2,3,3',4'-benzophenone dianhydride (6)

2,3,3',4'-Benzophenonetetracarboxylic acid (4) (3.7 g. 10 mmol) was suspended in minimum amount of acetic anhydride (3 g. 2.7 ml) and heated to reflux for 4 hours. The reaction mixture was cooled to room temperature. The corresponding dianhydride precipitated out and was collected and washed with ether to remove trace of acetic acid before drying under vacuum to afford 2.9 g (90%) of a-BTDA.

As shown in Example I and in Scheme III, the preparation of a-BTDA and a-6FDA presents a successful and economical synthesis of asymmetrical 2,3,3',4'-benzophenone dianhydride (a-BTDA) that can be formulated into low-melt viscosity polyimide resins (10-30 poise) that are amenable to low-cost resin transfer molding (RTM) process. Because a-BTDA is an isomer of s-BTDA used in PMR-15, essentially, this invention will afford an RTMable PMR-15 without health hazards associated with PMR-15 composites manufacturing. Additionally, the intermediate 2,3,3',4'-tetramethylbenzophenone also can be used to make asymmetrical 6F-dianhydride. This process can produce asymmetrical 6F-dianhydride (a-6FDA) to yield low viscosity 6F-polyimide resins adaptable to RTM process with potential 30% savings in manufacturing cost. Since this invention can produce novel a-BTDA and a-6FDA exclusively, it's essentially capable of producing a new class of thermoplastic and thermoset polyimides that have the potential of making colorless polyimides for optical and electronic applications.

While this invention has been described by a number of specific examples, it is obvious that there are other variation and modification that can be made without departing from the spirit and scope of the invention as set forth in the appended claims.

The invention claimed is:

1. Process for preparing 2,3,3',4'-tetramethylbenzophenone which comprises cross-coupling a boronic acid selected from the group consisting of 2,3-dimethylphenylboronic acid and 3,4-dimethylphenylboronic acid with a benzoic acid selected from the group consisting of 3,4-dimethylbenzoic acid and 2,3-dimethylbenzoic in the presence of a compound selected from the group consisting of:

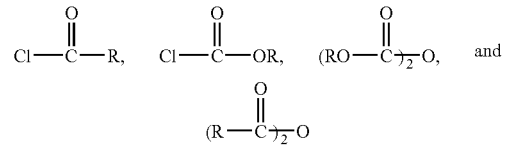

wherein R is a primary, secondary or tertiary lower alkyl group having 1 to 6 carbon atoms, and in the presence of catalysts and ligands to obtain coupled asymmetric 2,3,3',4'-tetramethylbenzophenone.

2. The process of claim 1 wherein a compound is added to the coupling reaction selected from the group consisting of water, KI, KF, K$_3$PO$_4$, K$_2$CO$_3$, Na$_2$CO$_3$, NaI, NaF, and N,N'-dicyclohexylcarbodiimide.

3. The process of claim 2 wherein the catalyst is palladium and the ligand is selected from the group consisting of PPh$_3$, PCy$_3$, P(p-MeOC$_6$H$_5$)$_3$, P(o-Tol)$_3$, and 1,1'-bis(diphenylphosphino)ferrocene (DPPF).

4. The process of claim 1 wherein the 2,3,3',4'-tetramethylbenzophenone is oxidized to obtain asymmetrical 2,3,3',4'-benzophenone tetracarboxylic acid.

5. The process of claim 4 wherein the 2,3,3',4'-benzophenone tetracarboxylic acid is converted to asymmetric 2,3,3',4' benzophenone dianhydride.

6. The process of claim 5 wherein the 2,3,3',4'-benzophenone tetracarboxylic acid is converted to asymmetric 2,3,3',4'-benzophenone diahydride by dehydration or chemical method.

7. The process of claim 1 wherein the 2,3,3',4'-tetramethylbenzophenone is reacted with trifluoromethyltetramethyl silane followed by hydrolysis to obtain 3,4'-(trifluoromethylmethanol)bis-o-xylene, subsequently reacting said bis-o-xylene with HX and CF$_3$X wherein X is halogen to obtain 3,4'-(hexafluoroisopropylidene)bis-o-xylene which is subsequently oxidized to obtain 3,4-(hexafluoroisopropylidene)diphthalic acid.

8. The process of claim 7 wherein the 3,4-(hexafluoroisopropylidene)dipthalic acid is converted to the asymmetric 3,4'-(hexafluoroisopropylidene)diphthalic anhydride.

9. The process of claim 8 wherein the 3,4'-(hexafluoroisopropylidene)diphthalic acid is converted to the asymmetric 3,4'-(hexafluoroisopropylidene)diphthalic anhydride by thermal dehydration or chemical method.

* * * * *